(12) United States Patent
Heeg et al.

(10) Patent No.: US 7,311,435 B2
(45) Date of Patent: Dec. 25, 2007

(54) SHAKING INCUBATOR

(75) Inventors: Hubert Heeg, Mömbris (DE); Stefan Betz, Erlensee (DE); Achim Melching, Langenselbold (DE)

(73) Assignee: Thermo Electron Led GmbH, Langenselbold (DE)

( * ) Notice: Subject to any disclaimer, the term of this patent is extended or adjusted under 35 U.S.C. 154(b) by 0 days.

(21) Appl. No.: 10/763,282

(22) Filed: Jan. 26, 2004

(65) Prior Publication Data
US 2004/0170082 A1 Sep. 2, 2004

(30) Foreign Application Priority Data
Jan. 24, 2003 (DE) ................. 103 02 809

(51) Int. Cl.
*B01F 11/00* (2006.01)
(52) U.S. Cl. ............... 366/109; 366/110; 366/209; 366/198; 366/218; 422/99
(58) Field of Classification Search .............. 366/109, 366/110, 111, 198, 218, 209; 422/69, 99
See application file for complete search history.

(56) References Cited

U.S. PATENT DOCUMENTS

| 863,009 | A | * | 8/1907 | Supper | 366/110 |
| 4,419,938 | A | * | 12/1983 | Kaut | 108/190 |
| 4,719,087 | A | * | 1/1988 | Hanaway | 422/102 |
| 4,921,676 | A | * | 5/1990 | Otani | 422/100 |
| 5,332,549 | A | * | 7/1994 | MacIndoe, Jr. | 422/63 |
| 5,346,303 | A | * | 9/1994 | Heinonen et al. | 366/208 |
| 5,372,425 | A | * | 12/1994 | Tannenbaum et al. | 366/208 |
| 5,431,201 | A | * | 7/1995 | Torchia et al. | 366/211 |
| 6,247,770 | B1 | * | 6/2001 | Glass | 312/263 |
| 6,659,637 | B2 | * | 12/2003 | Friedman | 366/110 |
| 6,808,304 | B2 | * | 10/2004 | Gebrian et al. | 366/110 |
| 2001/0019705 | A1 | * | 9/2001 | Ruediger et al. | 422/100 |
| 2002/0063077 | A1 | | 5/2002 | Ferger et al. | 206/449 |
| 2003/0215357 | A1 | * | 11/2003 | Malterer et al. | 422/50 |
| 2005/0115325 | A1 | * | 6/2005 | Felkins | 73/665 |

FOREIGN PATENT DOCUMENTS

| EP | 0 569 214 A2 | 11/1993 |
| EP | 0 569 214 A3 | 11/1993 |
| WO | WO 98/05753 | 2/1998 |

OTHER PUBLICATIONS

European Search Report dated Jun. 15, 2004.

* cited by examiner

*Primary Examiner*—Tony G. Soohoo
(74) *Attorney, Agent, or Firm*—Baker & Hostetler LLP

(57) ABSTRACT

The invention relates to a shaking incubator with at least one specimen storage device comprising several superposed specimen storage spaces. A shaking unit comprising a specimen storage position, a shaking platform and a base unit is arranged in at least one specimen storage space. The invention makes it possible to shake different specimens, located in the same specimen storage device, individually and independently of each other under incubator conditions.

21 Claims, 2 Drawing Sheets

SHAKING INCUBATOR

FIELD OF THE INVENTION

The invention relates to a shaking incubator with at least one specimen storage device comprising several superposed specimen storage spaces.

In the present context, the term "specimen storage device" denotes a device that can receive specimens in several specimen storage spaces superposed like a tower. In the following, the term "specimens" means open dishes, closed containers, so-called microtiter plates and similar containers for receiving specimens. These specimens are frequently used in research and industrial production in particular.

BACKGROUND OF THE INVENTION

Shaking incubators are basically known from the literature. Thus, European Patent Application EP 0569214 A2 discloses a shaker/incubator comprising an even number of shaking planes arranged like a tower that can be caused to shake by an eccentric drive. The significant disadvantage of this device is that all shaking planes are moved simultaneously by a common eccentric drive. Thus, it is impossible to move individual superposed shaking planes while other shaking planes of the tower are at rest. Also, the eccentric drive permits only the same intensity of shaking movement for all shaking planes of the tower.

SUMMARY OF THE INVENTION

The invention therefore is based on the problem of specifying a shaking incubator of the initially mentioned type that makes it possible to shake the specimens located in a specimen storage device individually and independently of each other.

This problem is solved for an initially characterized shaking incubator in that a shaking unit comprising a specimen storage position, a shaking platform, and a base unit is arranged in at least one specimen storage space.

The shaking unit arranged at a specimen storage space of a specimen storage device permits a specimen located at the specimen storage position of the shaking unit to be shaken individually according to a fixed motion sequence. If a shaking unit is arranged in several specimen storage spaces of a specimen storage device, the specimens located at the specimen storage positions of the shaking units can be agitated independently of each other according to a motion sequence determined individually for each specimen.

Preferred embodiments of the invention are indicated in the subordinate claims.

In a first preferred embodiment of the invention, the base unit of the at least one shaking unit is permanently connected to the specimen storage device. This assures on the one hand a permanent and especially stable fastening to the specimen storage device, and produces on the other hand an additional stabilization of the specimen storage device.

On the other hand, an alternative preferred further development provides a detachable holder for the at least one shaking unit of a specimen storage device in a specimen storage space so that the shaking unit can be removed as required from the specimen storage device. Basically, all detachable holders known in the prior art can be considered. For example, the shaking unit can be held on the specimen storage device, by two rails and sliding of the shaking unit can be prevented by a detachable snap connection.

In addition, it is advantageously provided that the specimen storage positions for the at least one shaking unit be designed such that a specimen can be supplied by an automated transport system, and a specimen can be removed from the specimen storage position by an automated transport system.

To this end, a preferred embodiment provides for the specimen storage position of the at least one shaking unit to comprise a spacer element arranged on the shaking platform which creates free space for manipulating a specimen located at the specimen storage position. The spacer element can have basically all forms known to a person skilled in the art. For example, a one-part, U-shaped spacer element or a spacer element consisting of two parts would be suitable. In both instances the spacer element is arranged on the shaking platform such that a specimen held on the bottom by a transport device can be placed without difficulty in the specimen storage position, and that the transport device can again be withdrawn.

It is also advantageous for the specimen storage position of a shaking unit to comprise at least one clamping element arranged on the shaking platform or on the spacer element. A specimen located in the specimen storage position can in this way be effectively prevented from sliding. The clamping element can be single or multi-part. For example, four fixing brackets at the corners of the specimen storage position are suitable for a multi-part clamping element.

In another preferred embodiment, a control unit for controlling and supplying current to the at least one shaking unit is arranged outside of the incubator workspace, with a control/supply line running from this control unit into the incubator workspace, said line having a line connector in the incubator workspace. The control unit comprises the components, known to a person skilled in the art, that are necessary to assure the current supply as well as the control of the at least one shaking unit in the incubator workspace. Thus, the control unit can comprise, e.g., a calculating unit by means of which the motion sequence of the shaking platform of a shaking unit is fixed.

The at least one shaking unit is advantageously connected via a detachable line connection to the line connector of the at least one control unit. A person skilled in the art is familiar with the various detachable line connections that can be used here.

In another preferred embodiment, a distributor unit for connecting several shaking units is arranged in the incubator workspace and is connected via a detachable line connection to the line connector of the at least one control unit. The distributor unit can be permanent or detachable, e.g., held on the wall of the incubator workspace. The line connector of the shaking units on the distributor unit can be permanent or detachable, according to the prior art. A detachable line connector between the shaking unit and the distributor unit is particularly appropriate when the shaking unit is to be removed as required from the specimen storage device.

An alternative preferred refinement provides for arranging a distributor unit on a specimen storage device. This minimizes the line length from the at least one shaking unit located in the specimen storage device to the distributor unit, and creates the possibility of replacing a specimen storage device rapidly and simply with another specimen storage device containing, e.g., a different number of shaking units in the specimen storage device. A replacement of the entire specimen storage device is advantageous, e.g., when the height of the specimens to be stored makes it necessary to change the number of specimen storage spaces present in a specimen storage device.

However, it can also be especially advantageous to arrange a distributor unit on several specimen storage devices for the connection of several shaking units. In particular, when numerous shaking units are present in several specimen storage devices, the line length from a shaking unit to the next distributor unit is kept as small as possible, and in addition it becomes more convenient to replace individual specimen storage devices.

Moreover, a preferred refinement provides for using of a shaking unit in which the shaking platform is positioned automatically in a central zero position after the current has been turned off. As a result, a specimen located on the shaking platform is brought into a central and horizontal position after the end of the shaking procedure, this being is a prerequisite for automated supply to and removal from the specimen storage position by a transport device.

Finally, an especially advantageous embodiment provides for a shaking unit to be arranged in several specimen storage spaces, and for the shaking platforms of these shaking units to be controllable individually and independently of each other by the at least one control unit. "Individually and independently of each other" in this context means that the shaking movement, that is, e.g., the shaking frequency or the amplitude (shaking level), can be set and controlled for each individual shaking platform by the at least one control unit. This makes it possible to supply a specimen storage device with different specimens and to move them according to their individual requirements as regards shaking movement and shaking duration. If a shaking movement is not intended for a specimen, the specimen storage space of the shaking unit functions as a static storage space on account of the resting shaking platform. The person skilled in the art is familiar with numerous applications in which a specimen must be alternately shaken and stored, under incubation conditions, in a chronological sequence. Consequently, the invention creates the possibility of introducing several specimens by an automated transport system in a chronologically staggered manner into one and the same specimen storage device, and of shaking and storing the specimens under incubation conditions according to an individual program.

The invention is described in detail in the following using an embodiment, and making reference to two drawings.

DETAILED DESCRIPTION OF THE DRAWING

Figure 1:
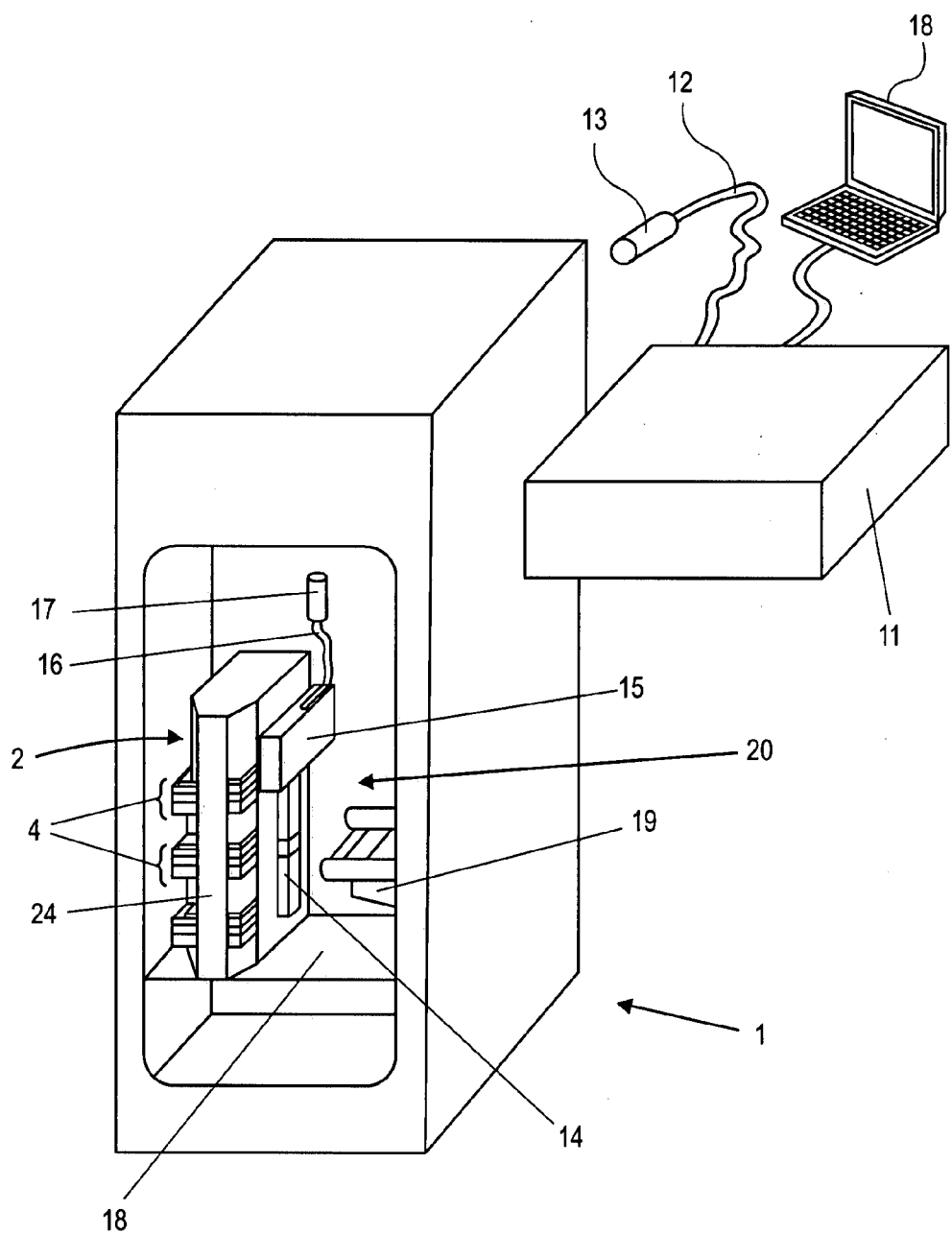
FIG. 1 shows an oblique rear view of a preferred embodiment of the invention.

FIG. 1 shows a shaking incubator 1 whose incubator workspace 20 can be viewed through the rear wall/door (not shown). Specimen storage device 2 comprising several superposed specimen storage spaces 3 (see FIG. 2) is shown in incubator workspace 20. A shaking unit 4 is arranged in each specimen storage space of illustrated specimen storage device 2. Shaking units 4 are connected to distributor unit 15 via line connections (not visible) located behind cover 14.

For its part, distributor unit 15 is detachably connected via line connection 16 and line connector 17 to line connector 13 of control/supply line 12 of control unit 11. In the present embodiment, control unit 11 comprises computer unit 18 that determines the shaking movement of shaking platform 6 of a shaking unit 4 located in specimen storage device 2. The communication of computer unit 18 with the other components of control unit 11 takes place in the present example via an RS282 interface. However, a person skilled in the art is basically familiar with other interfaces for this purpose.

Shaking incubator I shown in FIG. 1 comprises only one specimen storage device 2 that is arranged on mounting plate 18 in incubator workspace 20. However, a person skilled in the art is also familiar with arrangements of several specimen storage devices 2, also including a carousel-like arrangement like the one disclosed in WO 98/05753.

Device 19, partially shown, in incubator workspace 20 is a transport system known from the prior art, e.g., WO 98/05753. Specimens 10 can be moved with transport system 19 to the individual specimen storage spaces 3 of a specimen storage device 2 and placed there in a specimen storage position 5 (see FIG. 2). In a corresponding manner, a specimen 10 is removed again, as required, by transport system 19 from specimen storage position 5. According to the invention, the use of transport system 19 in the arranging of one or more shaking units 4 in specimen storage device 2 makes it possible to unite in a single incubator the advantages of automatic loading and unloading of specimen storage position 5 with specimens 10, and of automatic shaking of specimens 10.

Figure 2:
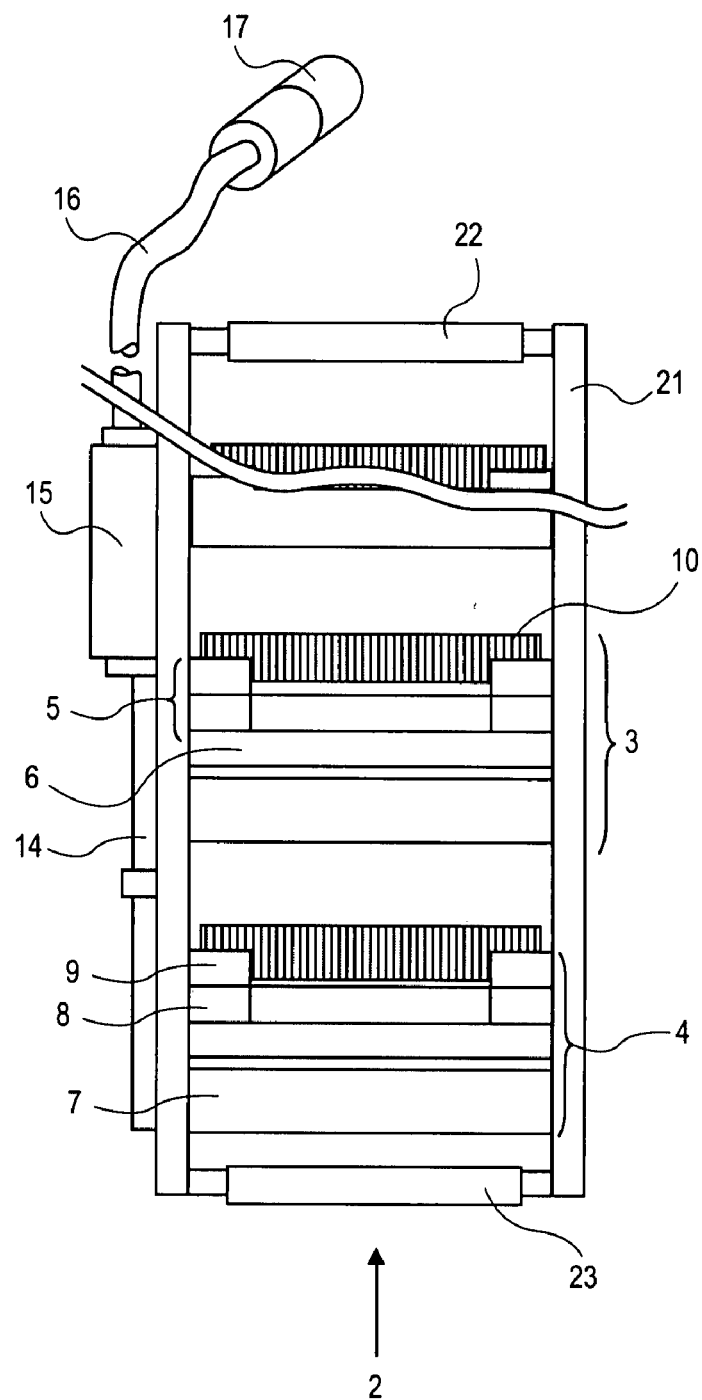
FIG. 2 shows a of the preferred embodiment of specimen storage device according to FIG. 1.

FIG. 2 shows a front view of a specimen storage device 2 in which a shaking unit 4 is arranged according to the invention in on at least one specimen storage space 3. The specimen storage device consists substantially of a tower-shaped construction with two side walls 21, cover plate 22 and bottom plate 23. Specimen storage device 2 is positioned reliably and protected against any sliding on mounting plate 18 with the aid of a centering opening (not shown) located in bottom plate 23 and with the aid of a centering strip (not shown) attached to mounting plate 18, this strip positively cooperating with the centering opening. In addition, specimen storage device 2 can comprise rear wall 24, as shown in FIG. 1, that imparts additional stability to the specimen storage device.

Typically, four to six shaking units 4 can be arranged in a specimen storage device 2, depending on the space requirement of the specimens to be stored. A shaking unit 4 comprises a specimen storage position 5, shaking platform 6, and base unit 7. As in the present embodiment, sliding of specimen 10 is effectively prevented by clamping elements 9. In the present instance, these elements are designed as fixing brackets at the four corners of specimen storage position 5. As can be seen from FIG. 2, specimen storage position 5 also comprises spacer element 8. This spacer element is arranged on shaking platform 6 and is designed such that transport system 19, holding specimen 10 from below, can place it onto a specimen storage position 5 and remove it again as required. In the case of a differently designed transport system that holds specimen 10, e.g., by its top, spacer elements 8 are not required. As FIG. 2 shows, specimen 10, clamping element 9 and spacer element 8 are arranged on shaking platform 6. That is, specimen 10 is moved together with specimen storage position 5 by shaking platform 6. The shaking movement of shaking platform 6 is produced by base unit 7 on which shaking platform 6 is arranged. Base unit 7 can be permanently connected to specimen storage device 2, as represented in the present embodiment, which results in additional stabilization of specimen storage device 2.

A specimen 10, shown in FIG. 2, is arranged together with clamping elements 9 and spacer element 8 on shaking platform 6 that is aligned relative to base unit 7 in a centered and parallel manner, that is, horizontally. Positioning of shaking platform 6 to a central zero position after the current has been turned off takes place automatically and without further external intervention. As a result, a specimen 10 comes to rest in a defined spatial position after the current has been turned off, without shaking platform 6 requiring a elaborate electrical tracking. A precisely known spatial position is necessary in order for automated transport system 19 to be able to take a specimen 10 from a specimen storage position 5 or place it in a specimen storage position 5.

Shaking units 4 of specimen storage device 2 shown in FIG. 2 are connected via line connections located under cover 14 to distributor unit 15 arranged on side wall 21 of specimen storage device 2. Distributor device 15 is connected by line connector 17 to line connector 13 of control unit 11. Thus, in the present embodiment all shaking units 4 located on the illustrated specimen storage device 2 are connected via only one detachable line connector 17 to control unit 11 serving for control and current supply.

As can be seen from FIG. 2, the interval between shaking units 4 located in specimen storage device 2 is selected such that specimens 10 even higher than the ones illustrated can be shaken. Concretely speaking, this means that in addition to the illustrated specimens 10 with a height of approximately 25 mm, even specimens up to a height of approximately 55 mm can be shaken. Since the height of shaking units 4 is known, and in the present embodiment is approximately 45 mm, it is possible at any time, using the aforementioned dimension data, to change the number of shaking units 4 in specimen storage device 2 so as to satisfy the particular requirements.

The invention claimed is:

1. An incubator, comprising:
   an incubator workspace disposed within the incubator;
   at least one specimen storage device disposed within the incubator workspace;
   a plurality of superposed shaking units located within the at least one specimen storage device, wherein each of the superposed shaking units comprises:
     a specimen storage position to receive one or more specimens;
     a horizontally disposed and individually controllable shaking platform coupled to the specimen storage position; and
     a base unit coupled to the shaking platform to produce a shaking movement to the shaking platform; and
   at least one control unit to control the shaking movement of the shaking platform of each of the plurality of shaking units, wherein the shaking movement of the shaking platform of each shaking unit is controlled independently of each other shaking unit by the at least one control unit.

2. The incubator according to claim 1, wherein the base unit of at least one of the plurality of shaking units is permanently connected to the specimen storage device.

3. The incubator according to claim 1, further comprising a detachable holder for at least one of the plurality of shaking units of the specimen storage device, wherein the at least one of the plurality of shaking units is removable from the specimen storage device.

4. The incubator according to claim 1, wherein the specimen storage position of at least one of the plurality of shaking units is supplied the one or more specimens by means of an automated transport system and the one or more specimens is removed from the specimen storage position by the automated transport system.

5. The incubator according to claim 4, wherein the specimen storage position of at least one of the plurality of shaking units comprises a spacer element, arranged on the shaking platform, to create a free space for manipulating, by the automated transport system, the one or more specimens located in the specimen storage position.

6. The incubator according to claim 5, wherein the specimen storage position of at least one of the plurality of shaking units comprises at least one clamping element arranged on the shaking platform or on the spacer element.

7. The incubator according to claim 1, wherein the at least one control unit controls and supplies current to the plurality of shaking units, and wherein the at least one control unit is arranged outside of the incubator workspace, and a control/supply line runs from the at least one control unit into the incubator workspace, the control supply line having a line connector in the incubator workspace.

8. The incubator according to claim 7, wherein at least one of the plurality of shaking units is connected via a detachable line connection to the line connector of the at least one control unit.

9. The incubator according to claim 7, further comprising a distributor unit for connecting the plurality of shaking units is arranged in the incubator workspace and is connected via a detachable line connection to the line connector.

10. The incubator according to claim 7, further comprising a distributor unit for connecting the plurality of shaking units is arranged on the specimen storage device.

11. The incubator according to claim 7, further comprising a distributor unit for connecting a plurality of shaking units is arranged on one or more of the specimen storage devices.

12. The incubator according to claim 1, wherein the shaking platform of one or more of the plurality of shaking units is configured to return to a central zero position after the power to the one or more of the plurality of shaking units has been turned off.

13. The shaking incubator according to claim 1, wherein the incubator workspace comprises a plurality of specimen storage spaces and one of the plurality of shaking units is arranged in each of the specimen storage spaces of the incubator workspace.

14. A shaking apparatus, comprising:
   a plurality of superposed shaking units located within a specimen storage device, wherein each of the superposed shaking units comprises:
     a base;
     a shaking platform coupled to the base;
     a spacer disposed above and coupled to the shaking platform;
     a clamping element coupled to the spacer; and
     a specimen storage unit removably coupled to the clamping element, wherein the specimen storage unit is configured to house one or more specimens; and
   a control unit to control the shaking movement of the shaking platform of each of the plurality of shaking units, wherein the shaking movement of the shaking platform of each shaking unit is controlled independently of each other shaking unit by the control unit.

15. The shaking apparatus of claim 14, wherein the base of one or more of the plurality of shaking units is configured to be permanently affixed to the specimen storage device housing the plurality of shaking units.

16. The shaking apparatus of claim 14, wherein the shaking platform is detachably coupled to the base.

17. The shaking apparatus of claim 14, wherein the spacer is configured to allow for an area in order to manipulate the one or more specimens located in the specimen storage unit.

18. The shaking apparatus of claim 14, wherein the control unit controls and supplies current to the plurality of shaking units, and wherein the control unit is configured to couple to a line connector to respectively connect to the plurality of shaking units.

19. The shaking apparatus of claim 18, wherein the control unit further comprises a detachable line connection configured to couple to the line connector to respectively connect to the plurality of shaking units.

20. The shaking apparatus of claim 14, wherein the plurality of shaking units are coupled together by a distributor unit and wherein a distributor line from the distributor unit couples to a detachable line connection of the control unit.

21. A shaking apparatus, comprising:
  a plurality of superposed shaking units located within a specimen storage device, wherein each of the superposed shaking units comprises:
    a base;
    a shaking platform coupled to the base;
    a specimen storage unit removably coupled to the shaking platform, wherein the specimen storage unit is configured to house at least one specimen; and
  a control unit to control the shaking movement of the shaking platform of each of the plurality of shaking units, wherein the shaking movement of the shaking platform of each shaking unit is controlled independently of each other shaking unit by the control unit.

* * * * *